United States Patent [19]

Raven et al.

[11] Patent Number: 4,994,058
[45] Date of Patent: * Feb. 19, 1991

[54] SURFACE SHAPING USING LASERS

[75] Inventors: Antony L. Raven, Hertfordshire; John Marshall, Hants, both of United Kingdom; David F. Muller, Boston, Mass.

[73] Assignee: Summit Technology, Inc., Watertown, Mass.

[*] Notice: The portion of the term of this patent subsequent to Aug. 15, 2006 has been disclaimed.

[21] Appl. No.: 124,101

[22] Filed: Jan. 15, 1988

[30] Foreign Application Priority Data

Mar. 19, 1986 [GB] United Kingdom ............... 8606821

[51] Int. Cl.$^5$ .............................................. A61N 5/06
[52] U.S. Cl. ......................................... 606/5; 128/375; 128/897; 128/898; 219/121.060; 219/121.073; 219/121.085; 350/363
[58] Field of Search ................. 128/303.1, 395, 347, 128/348, 897, 898; 606/5; 350/363; 219/121.60, 121.07, 121.68, 121.73, 121.85

[56] References Cited

U.S. PATENT DOCUMENTS

| | | | |
|---|---|---|---|
| 3,558,208 | 1/1971 | Hudson | 350/314 |
| 3,703,176 | 11/1972 | Vasilliadis et al. | 128/394 |
| 3,769,963 | 11/1973 | Goldman et al. | 128/2 R |
| 3,941,973 | 3/1976 | Luck, Jr. et al. | 219/121 |
| 3,982,541 | 9/1976 | L'Esperance, Jr. | 128/303.1 |
| 4,173,980 | 11/1979 | Curtin | 128/303 R |
| 4,266,549 | 5/1981 | Kimura | 128/303.1 |
| 4,309,998 | 1/1982 | Aaron nee Rosa et al. | 128/303.1 |
| 4,326,529 | 4/1982 | Doss et al. | 128/303.1 |
| 4,381,007 | 4/1983 | Doss | 128/303.1 |
| 4,461,294 | 7/1984 | Baron | 128/303.1 |
| 4,527,043 | 7/1985 | Hashiura et al. | 219/121 |
| 4,538,608 | 9/1985 | L'Esperance, Jr. | 128/303.1 |
| 4,648,400 | 3/1987 | Schneidere et al. | 128/303.1 |
| 4,665,913 | 5/1987 | L'Esperance, Jr. | 128/303.1 |
| 4,669,466 | 6/1987 | L'Esperance | 128/303.1 |
| 4,686,979 | 8/1987 | Gruen et al. | 128/303.1 |
| 4,732,148 | 3/1988 | L'Esperance, Jr. | 128/303.1 |
| 4,798,204 | 1/1989 | L'Esperance | 128/303.1 |
| 4,856,513 | 8/1989 | Muller | 606/5 |

FOREIGN PATENT DOCUMENTS

| | | |
|---|---|---|
| 111060 | 6/1984 | . |
| 152686 | 8/1985 | European Pat. Off. . |
| 3148748 | 7/1983 | Fed. Rep. of Germany . |
| 3535072 | 9/1987 | Fed. Rep. of Germany . |
| 3535073 | 9/1987 | Fed. Rep. of Germany . |
| WO86/04500 | 8/1986 | PCT Int'l Appl. . |

OTHER PUBLICATIONS

Fine et al., "Preliminary Observations on Ocular Effects...", vol. 64, No. 2, American Journal of Opthalmology, pp. 209-222 (Aug. 1967).
Beckman, et al., "Limbectomies, Keratectomies, and Keratostomies Performed.." vol. 71, American Journal of Opthalmology, pp. 1277-1283 (Jun. 1971).
Mainster, "Opthalmic Applications of Infrared Lasers—Thermal Considerations" vol. 18, No. 4, Invst. Ophthal. and Vis. Sci., pp. 414-420 (1979).
Peyman, et al, "Modification of Rabbit Corneal Curvature with use of Carbon Dioxide Laser Burns", vol. 11, No. 5, Ophthalmic Surgery, pp. 325-329 (May 1980).

(List continued on next page.)

Primary Examiner—Lee S. Cohen
Assistant Examiner—David Shay
Attorney, Agent, or Firm—Thomas J. Engellenner

[57] ABSTRACT

A laser system and masking apparatus for reprofiling surfaces, such as corneal surfaces. The system includes a laser and a mask disposed between the laser and the surface to be reprofiled, the mask providing a predefined profile of resistance to laser radiation, such that upon irradiation, part of the radiation is selectively absorbed and part is transmitted to the surface in accordance with the masked profile, to selectively erode the surface. The masking apparatus may consist of a mask to be affixed to the surface or may further include a support structure to support and position the mask above the surface. The resistance profile can be created by varying the thickness or the composition of the mask.

29 Claims, 4 Drawing Sheets

OTHER PUBLICATIONS

Keates et al., "Carbon Dioxide Laser Beam Control for Corneal Surgery", *Ophthalmic Surgery*, pp. 117-122, (Feb. 1981).

Girard, "Refractive Keratoplasty", vol. 2, *Corneal Surgery*, pp. 142-171 (1981).

Taboada et al., "Response of the Corneal Epithelium to KrF Excimer Laser Pulses", vol. 40, *Health Physics*, pp. 677-683 (May 1981).

Chetverukhin et al., "Refraction Thermokeratoplasty and and Laser Keratoplasty", *Vestn. Oftal.*, pp. 67-69 (USSR 1982).

Srinivasan et al., "Far-UV Photoetching of Organic Material", *Laser Focus*, (May 1983).

Srinivasan, "Kinetics of the ablative photodecomposition of organic polymers . . .", vol. B1, *J. of Vac. Sci. Technol.*, pp. 923-926 (1983).

Srinivasan, "Action of Far-Ultraviolet Light on Organic Polymer Films . . .", pp. 12-14 (Oct. 1983).

Troke, et al. "Excimer Laser Surgery of the Cornea", vol. 96, *American Journal of Opthalmology*, pp. 710-715 (1983).

Galbavy, "Use of Diamond Knives in Ocular Surgery", vol. 15, No. 3, *Opthalmic Surgery*, pp. 203-205 (Mar. 1984).

Puliafito et al., "Excimer Laser Ablation of the Cornea and Lens", vol. 92, No. 6, *Opthalmology*, pp. 741-748 (Jun. 1985).

L'Esperance, Jr., "New laser systems and their potential clinical usefulness", *Trans. New Orleans Acad. of Opthalmol.*, pp. 182-209 (1985).

L'Esperance, Jr., "Current Status of Ophthalmic Photovaporization Therapy", *Trans. New Orleans Acad. of Opthalmol, pp. 231-255 (1985).*

O'Hara et al., vol. 11 *IBM Technical Disclosure Bulletin*, pp. 1168-1169 (1969).

Photoablative reprofiling of the Cornea using an Ecimer Laser: Photorefractive Keratectomy; Marshall et al; Lasers in Opthal. vol. 1, No. 1, pp. 21-48 1986.

SURFACE SHAPING USING LASERS

REFERENCE TO RELATED APPLICATIONS

This application is a continuation-in-part of U.S. Ser. No. 19,200 filed Mar. 9, 1987 now U.S. Pat. No. 4,856,513.

DESCRIPTION

1. Field of the invention

This invention relates to apparatus and method employing lasers, especially pulsed lasers, for shaping surfaces, especially surfaces of organic material. In particular, the invention relates to apparatus and methods for shaping biological tissue, including the cornea of the eye.

BACKGROUND OF THE INVENTION

It is known to employ a laser source to erode surfaces of workpieces and the like. Such apparatus is in general relatively complex and demands highly skilled use. It is an object of the present invention to provide improved and simplified apparatus and method for eroding surfaces.

It is also an object of the present invention to provide an improvement whereby laser techniques can be applied to sensitive surfaces and in particular to objects in which it would be undesirable to affect underlying layers.

In the field of medicine, a known technique for the treatment of certain forms of myopia is surgically to remove a segment of the collagen sub-surface layer of the eye, to reshape the removed segment as by surgical grinding, and to restore the reshaped segment in the eye. The eye heals by reformation of the outer cellular layer over the reshaped collagen layer. Alternatively, a layer of the cornea is opened up as a flap, an artificial or donor lenticular implant is inserted under the flap, and the flap is sutured up again.

It is a further object of this invention to provide an improved and less traumatic method and apparatus for reshaping the cornea of the eye.

Various other surgical techniques for reprofiling of the corneal surface have also been proposed. One increasingly common technique is radial keratotomy, in which a set of radial incisions, i.e. resembling the spokes of a wheel, are made in the eye to remedy refractive errors such as myopia (nearsightedness). As the incisions heal, the curvature of the eye is flattened, thereby increasing the ocular focal distance. The operation is not particularly suitable for correction of hyperopia (farsightedness) and can pose problems if the surgical incisions are uneven or too deep.

The use of a laser beam as a surgical tool for cutting incisions, a so-called "laser scalpel", has been known for some time (see for example U.S. Pat. No. 3,769,963 to Goldman et al). In 1980, a study was made of the damage which might be inflicted on the corneal epithelium by exposure to the recently developed excimer laser (see Taboada et al, "Response of the Corneal Epithelium to ArF excimer laser pulses" *Health Physics* 1981, Volume 40, pp 677–683). At that period, surgical operations on the cornea were commonly carried out using diamond or steel knives or razor, and further such techniques were still being studied (see for example Binder et al, "Refractive Keratoplasty" *Arch, Ophthalmol.* May 1982, Vol. 100, p 802). The use of a physical cutting tool in corneal operations, and the insertion of an implant under a flap, continue to be widely practised and techniques further developed up to the present day (see for example "Refractive Keratooplasty improves with Polysulfone, Pocket Incision" *Ophthalmology Times,* July 1, 1986).

It has been suggested in European Patent Application No. 01518699 of L'Esperance, to perform controlled ablative photodecomposition of one or more selected regions of a cornea using a scanning action on the cornea with a beam from an excimer laser. Because of the scanning action, it is necessary for L'Esperance to bring his laser beam to a small spot, typically a rounded-square dot of size 0.5 mm by 0.5 mm.

L'Esperance suggests that myopic and hyperopic conditions can be reduced by altering the curvature of the outer surface of the cornea by repeatedly scanning the cornea with an excimer laser beam having this standard small spot size by varying the field which is scanned during successive scans, so that some areas of the cornea are scanned more often than others. In this way, it is claimed that the surface can be eroded by different amounts depending on the number of times they are scanned by the spot. Additionally, he suggests that certain severe myopic and hyperopic conditions may be treated with a reduced removal of tissue by providing the outer surface of the cornea with a new shape having Fresnel-type steps between areas of the desired curvature.

In practice, complex apparatus is required to cause a laser beam to scan with the precision required if the eroded surface is to be smooth. Thus, if successive sweeps of a scan overlap, there will be excessive erosion in the overlap area, whereas if they fail to meet, a ridge will be left between the sweeps. The compression of the excimer laser beam to a small spot will increase the beam energy density, which will tend to exacerbate these problems. It is not clear that L'Esperance has found a suitable scanning system, since in one embodiment he attempts to control the laser beam by a magnetic field.

Additionally, the scanning method is inherently time-consuming even with highly refined techniques and apparatus, since the laser beam is only eroding a very small part of the total area to be treated at any given moment. Furthermore, such a scanning system can cause rippling effects on relatively soft materials such as corneal tissue.

It is therefore a further object of the present invention to provide a method and apparatus for eroding a surface using a laser which does not require scanning of the area of the surface to be eroded.

Another technique for corneal reshaping, described in British Patent Application No. 8604405 and herein incorporated by reference, involves the use of a laser photoablation apparatus in which the size of the area on the surface to which the pulses of laser energy are applied, is varied to control the reprofiling operation. In one preferred embodiment, a beam-shaping stop or window is moved axially along the beam to increase or decrease the region of cornea on which the laser radiation is incident. By progressively varying the size of the exposed region, a desired photoablation profile is established in the surface. For further details on this technique, see also, Marshall et al, "Photo-Ablative Reprofiling of the Cornea Using an Excimer Laser: Photorefractive Keratoctomy", Vol. 1, *Lasers in Ophthalmology,* pp 21–48 (1986).

Although this technique for varying the size of the exposed region is a substantial improvement over physical shaping (i.e. scalpel) techniques and laser spot scanning protocols, a considerable number of optical elements and control systems still are required for precise operation, particularly on human corneal tissue. There exists a need for better and simpler procedures for shaping surfaces, particularly the surfaces of biological tissues, such a corneal tissue.

THE INVENTION

According to one aspect of the present invention, there is provided, a laser apparatus for reprofiling a surface comprising, a laser means, control means for controlling the laser to project laser radiation towards the surface, and a masking means disposed between the laser means and the surface having a predefined profile of resistance to the laser radiation, so that upon irradiation of the masking means, a portion of the laser radiation is selectively absorbed and another portion is transmitted to the surface, in accordance with the mask profile, to selectively erode the surface.

The masking means may be formed from material which is ablated by absorption of the laser radiation so that the masking means is progressively destroyed during the surface reprofiling.

Alternatively the masking means may be formed from material which has differing transmission characteristics over the masked area but which is not substantially ablated or otherwise eroded during the surface reprofiling.

The masking means may comprise a lens-like device which is supported by a rigid structure which is affixed to the surface, (for example to the sclera of an eye where the apparatus is to be used in conjunction with corneal surgery), the lens being connected to the support structure and disposed above the surface either in contact with the surface or a small distance thereabove. The lens can be directly integrated with the support structure or, preferably, the support structure may include a transparent stage to support and position the lens.

In another embodiment, the masking means may comprise a contact-type lens device which is disposed upon, and directly affixed to, the surface (e.g. the cornea of an eye in the case of corneal surgery). Typically the contact-type lens is constructed so as to have a first surface contoured to fix to the surface to be eroded and a second surface contoured to provide the desired surface contour following erosion by exposure to laser radiation.

In a further embodiment the masking means may comprise a tray or well of optically transparent material in which a quantity of a selected masking material in the form of a liquid or gel or gas or vapour or volatile material can be contained. The base of the tray or well may be curved so that the underside of the masking material contained therein is either convexly or concavely shaped to define a "lens". By choice of material so the absorption of the laser light by the masking material will cause selective erosion of the surface below the tray or well. The latter may be supported on or above the surface and may be in contact with the surface if desired.

Whichever is selected, a masking lens of the present invention provides a predefined profile or resistance to erosion by laser radiation. Such profiles can be provided by varying the thickness or composition of the lens material. When the thickness of the lens if varied, and dependent on the nature of the erosion of the object which is required, the lens may be convexo-concave, plano-convex, plano-concave, convexo-convex or concavo-concave, and it may also be aspheric or torroidal at least on one surface. In special cases the surface shape may be irregular, as might be required in the case of surgery on a cornea to remove an ulcer.

Conveniently the lens material has similar ablation characteristics to the surface material. Various polymeric materials can be employed including, for example, polymethylmethacrylate, polymethylstyrene and mixtures thereof. For corneal reprofiling, the ablation characteristics of the masking material can range from about $10^3$ to about $10^6$ cm$^{-1}$. Preferably, the masking material has an absorption characteristic of micron or submicron etch depths per pulse similar to those of the cornea when it is exposed to pulsed UV excimer laser radiation.

According to another aspect of the invention, there is provided a method of reprofiling a surface comprising (a) locating a laser means relative to an optical axis of a surface, the laser means being operable to deliver laser radiation to the surface; and (b) disposing a masking means between the laser means and the surface, the masking means having a predefined profile of resistance to the laser radiation, and (c) irradiating a portion of the radiation is selectively absorbed and another portion is transmitted to the surface in accordance with the mask profile, to selectively erode the surface.

The method may include varying the thickness of the masking means or varying the composition of the masking means, to provide the desired resistance profile.

Typically, the laser is set to operate so that a single pulse erodes a depth in the range 0.1 to 1 micrometer of surface material.

The method may be applied to any ablatable surface including biological tissue such as a ligament or a cartilage in a bone.

The method of the present invention is particularly well suited for controlled reprofiling of the cornea, particularly the collagen sub-layer thereof which lies immediately below the uniform, extremely thin, epithelial layer of the cornea, which is very rapidly ablated on exposure to the laser light. The extremely thin surface layer heals and eventually reforms following the re-shaping operation. In surgical applications, the laser light is of a wavelength obtainable from a UV Argon Fluoride laser, typically about 193 nanometers, which does not penetrate through the cornea. A minimum laser irradiance level is essential for ablation, but it is preferred not greatly to exceed this minimum threshold.

The pulse repetition rate for the laser may be chosen to meet the needs of each particular application. Normally, the rate will be between 1 and 500 pulses per second, preferably between 1 and 100 pulses per second.

Suitable irradiation intensities vary depending on the wavelength of the laser, and the nature of the irradiated object. For any given wavelength of laser energy applied to any given material, there will typically be a threshold value of the energy density below which significant erosion does not occur. Above the threshold density, there will be a range of energy density over which increasing energy densities give increasing depths of erosion, until a saturation value is reached.

For increases in energy density above the saturation value, no significant increase in erosion occurs.

The threshold value and the saturation value will vary from wavelength to wavelength of laser energy and from material to material of the surface to be eroded. However, for any particular laser and any particular material, the values can be found readily by experiment. For example, in the case of eroding a mask and the underlying corneal stroma (collagen sub-layer) by energy of wavelength 193 nm (the wavelength obtained from an ArF excimer laser), the threshold value is about 50 mJ per cm$^2$ per pulse, and the saturation value is about 250 mJ per cm$^2$ per pulse. There appears to be little benefit in exceeding the saturation value by more than a small factor, and suitable energy densities at the corneal surface are 50 mJ per cm$^2$ to 1 J per cm$^2$ per pulse for a wavelength of 193 nm.

The threshold value can vary very rapidly with wavelength, and at 157 nm, which is the wavelength obtained from an F$_2$ laser, the threshold is about 5 mJ per cm$^2$ per pulse. At this wavelength, suitable energy densities at the corneal surface are 5 mJ per cm$^2$ to one J per cm$^2$ per pulse.

Most preferably, the laser system is used to provide an energy density at the surface to be eroded of slightly less than the saturation value. Thus, when eroding the cornea with a wavelength of 193 nm (under which conditions the saturation value is 250 mJ per cm$^2$ per pulse), it is preferable to provide to the erodable mask and cornea pulses of an energy density of 100 to 150 mJ per cm$^2$ per pulse. Typically, a single pulse will erode a depth in the range 0.1 to 1 micrometer of collagen from the cornea.

The invention also lies in a system for reprofiling a surface using laser radiation in which masking means is disposed between the source of laser radiation and the surface for providing a predefined profile of resistance to the said laser radiation, such that upon irradiation of the masking means a portion of the laser radiation is selectively absorbed and another portion is transmitted to the surface, in accordance with the mask profile, to selectively erode the surface.

The surface which undergoes erosion may be biological tissue, particularly corneal tissue, and may include means to immobilise the surface.

The masking means may include a rigid support structure affixed to the surface with a masking lens connected to the support structure and disposed above the surface. The support structure further may include a transparent stage with the masking lens affixed to the stage. The masking lens may vary in thickness, or may vary in composition to provide the predefined profile of resistance.

The lens may be formed from polymethylmethacrylate, polymethylstyrene, or mixtures thereof.

The masking means may include a masking lens disposed upon, and directly affixed to, the cornea, which as above described may vary in thickness or in composition, to provide the predefined profile of erosion resistance. As before the lens may be formed from polymethylmethacrylate, polymethylstyrene, or mixtures thereof.

The laser source may be a pulsed excimer laser, typically an Argon-Fluoride laser operating at a wavelength of about 913 nanometers.

The invention also lies in masking apparatus for use in laser reprofiling of corneal tissue comprising a rigid support structure adapted for fixation upon a cornea, and a mask connected to the support structure and disposed above the cornea, the mask having a predefined profile of resistance to the laser radiation, whereby upon irradiation of the mask, a portion of the laser radiation is selectively absorbed and another portion is transmitted to the cornea in accordance with the mask profile to selectively erode the tissue.

The support may include a transparent stage adapted to receive the mask.

The mask may comprise a lens which varies in thickness or composition, to provide the profile.

The mask may be formed from polymethylmethacrylate, polymethylstyrene, or mixtures thereof.

The invention also lies in masking apparatus for use in laser reprofiling of corneal tissue comprising a masking lens adapted for direct fixation upon a cornea, the lens having a predefined profile of resistance to erosion by laser radiation, whereby upon irradiation of the lens, a portion of the laser radiation is selectively absorbed and another portion is transmitted to the cornea in accordance with the lens profile to selectively erode the tissue.

The lens may have a diameter in the range of about 3 to 12 millimeters and a maximum thickness of about 2 millimeters or less, and may vary in thickness, or in composition to provide the profile.

The masking means may be secured to the cornea by a suction means and a vacuum pump may be provided to reduce the pressure within the suction means, to fix the suction means in place on the cornea. As before the lens may be formed from polymethylmethacrylate, polymethylstyrene, or mixtures thereof, or the lens may be formed by a mass of material contained in a well or dish, above the cornea, which is optically transparent to the laser radiation.

The well or dish may include a transparent lid or cover, and the well or dish may be a liquid or gel, or gas or a vapour.

The apparatus may be formed at least in part from a material which is ablated or eroded by the laser radiation, said resistance being a measure of the resistance to ablation or erosion by the laser radiation.

The rate of ablation or erosion for the lens material may be substantially the same on the rate of ablation or erosion of the corneal surface.

The invention will next be described in connection with certain illustrated embodiments; however, it should be clear that those skilled in the art can make various modifications, additions and subtractions without departing from the spirit or scope of the invention. For example, the invention can be used in connection with corneal transplants where a donor insert is stitched into the patient's eye. Quite often, accidental overtightening of the stitches introduces refractive errors in the cornea following the operation. At present, the transplant operation must be repeated or relaxing incisions must be made in the cornea. The present invention can provide an improved and less traumatic method for remedying such refractive errors.

Additionally, the present invention can be applied to the remedy of stigmatisms, corneal ulcers and keratomic growths which affect vision. In such instance, specific masks can be designed and constructed to selectively remove the corneal tissue which interfere with normal refraction.

Moreover, the teaching of the present invention can be applied to other biological tissues requiring reprofiling including, for example, ligaments, cartilage, and bone.

DESCRIPTION OF THE DRAWINGS

The invention will now be described by way of example with reference to the accompanying drawings, in which.

DETAILED DESCRIPTION OF ILLUSTRATED EMBODIMENTS

Figure 1:
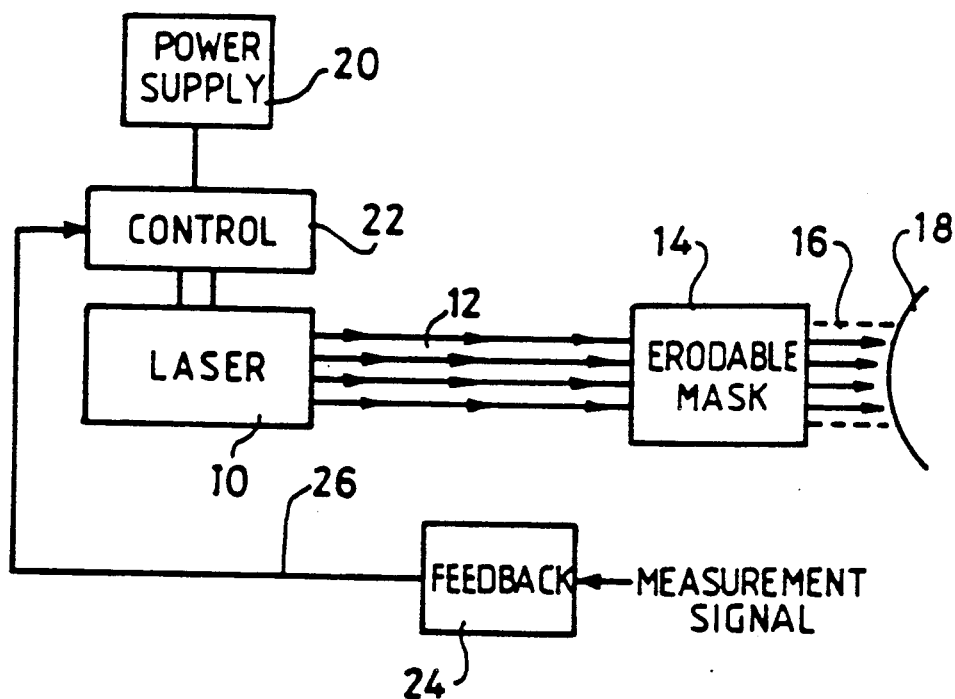
FIG. 1 is a diagrammatic illustration of an apparatus for practicing a method of reprofiling the surface of an object, in accordance with the invention.

In FIG. 1, a laser 10 provides a radiation output 12 to an erodable mask 14 which provides a predefined profile of resistance to the radiation. A portion of the laser radiation 16 is selectively transmitted in accordance with the profile of mask 14 and irradiates the surface 18 of the object which is to be reprofiled and which as shown may comprise the cornea of an eye.

The laser is powered by a power supply unit 20 and control circuit 22 which can be adjustable to cause the laser to produce pulses of light at a specific frequency and intensity. To further control the laser, a feedback device 24 can be provided which receives information from optical or other inspection of the mask 14 and/or surface 18 while it is exposed to irradiation by the laser 10. A feedback path 26 communicates with the control circuit 22 for controlling the laser 10.

Figure 2:
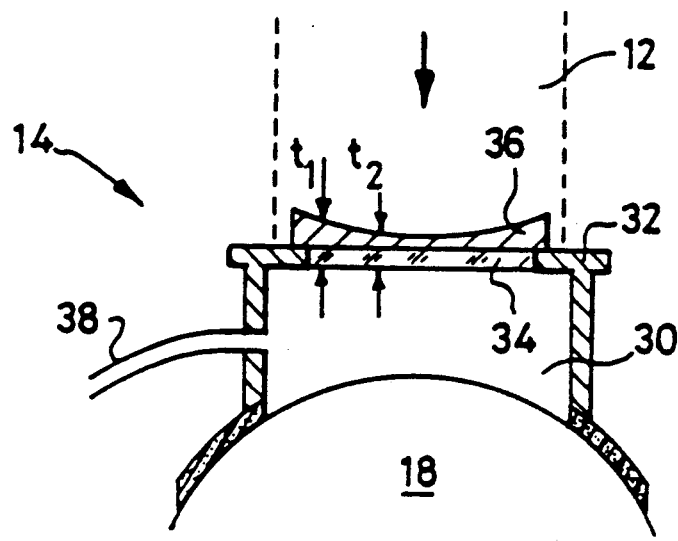
FIG. 2 is a more detailed illustration of an erodable mask suitable for use in the apparatus of FIG. 1.

In FIG. 2, one embodiment of the erodable mask 14 of FIG. 1 is shown in more detail. As illustrated, the erodable mask 14 includes a suction cup 30 which provides a support structure having rigid vertical walls and a horizontal surface 32. At least a portion of the horizontal surface 32 is formed by a transparent stage 34. Preferably, the remainder of surface 32 is opaque to laser radiation. Disposed upon the transparent stage 34 is masking lens 36.

The entire structure can be placed upon the surface of the object, i.e. the sclera of an eye, leaving the corneal surface 18 unobstructed. A flexible tube 38 supplies vacuum suction to the cup, so as to clamp it to the eye with a force sufficient to hold it in place but not distort the shape of the cornea.

The erodable mask 14 can be rigidly connected to the laser or otherwise optically aligned therewith such that pulsed radiation from the laser can be selectively transmitted through the mask to produce the desired erosion of the surface.

Figure 3:
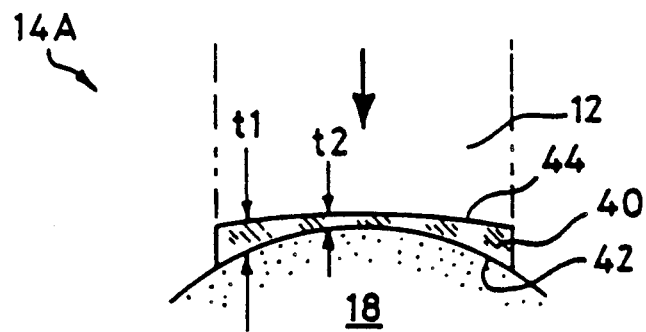
FIG. 3 is an illustration of alternative embodiment of an erodable mask suitable for use in the apparatus of FIG. 1.

In FIG. 3, an alternative embodiment of the invention is shown wherein an erodable mask 14A is formed by a contact-type lens 40 fitted to the object, i.e. the surface of an eye 18 over the area to be treated. As in FIG. 2, the lens 40 is uniformly irradiated with a pulsed beam of light 12 obtained from a laser radiation source.

The lens, as fitted, has a lower surface 42 of a shape matching the existing contour of the object and an upper surface 44 matching the shape of the object desired after reprofiling.

Both lens 36 of FIG. 2 and lens 40 of FIG. 3 illustrate how the erodable mask can vary in thickness to provide a predefined profile of resistance. The selected lens material is a material which is erodable by laser radiation and preferably has ablation characteristics substantially identical to the object material. Most preferably, the maximum thickness $t_1$ of the lens exceeds the minimum thickness $t_2$ by an amount approximately equal to the maximum depth $d$ of erosion required to complete the reprofiling of the surface.

For example, the erodable masks of the present invention can be formed from plastics material such as poly(methylpethacrylate) (PMMA) or poly(methyl styrene) (PS). These polymers are both bio-compatible and can be efficiently eroded by laser radiation, i.e. by a pulsed ArF excimer laser (193 nm). These polymers are mutually soluble in each other, and by changing the concentration of PS in PMMA, absorption coefficients can be varied from about $10^3$ to about $10^6$ cm$^{-1}$. Other organic polymers exhibiting suitable ablation characteristics can also be employed in the manufacture of erodable masks. For use in corneal surgery the polymeric material preferably has an absorption characteristic of micron or submicron etch depth per pulse, similar to the absorption characteristics of the cornea. For further details on organic polymers suitable for construction of masks, see Cole et al, "Dependence of Photoetching Rates of Polymers at 193 nm on Optical Absorption Coefficients", Vol. 48 *Applied Physics Letters*, pp 76–77 (1986), herein incorporated by reference.

Various techniques can be employed to manufacture the lenses used in the present invention from PMMA or PS. These techniques included injection moulding, casting, machining and spin casting. Manufacture by laser machining can also be employed. In one typical technique, a solution of PMMA or PS is prepared in toluene and spin cast in a suitably-shaped cup to obtain a smooth, uniform lens having a pre-defined profile thickness. Depending upon the concentration of PS in PMMA, a suitable absorption coefficient is obtained. The films can then be removed from the spin cup and vacuumed baked to residual solvent.

Alternatively, the erodable mask can be made of a material having a variable composition such that predefined regions of the mask selectively absorb greater amounts of laser radiation even though the entire mask has a uniform thickness. Again, materials such as PMMA and PS can be employed in varying concentrations in the erodable mask to achieve the variable composition of the mask.

Figure 4A:
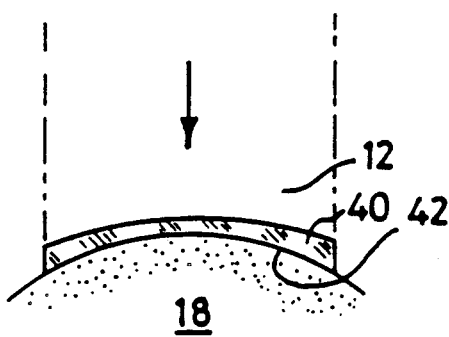
FIG. 4A illustrates diagramatically the beginning of a reprofiling operation to reduce the curvature of an object in accordance with the present invention.
Figure 4B:
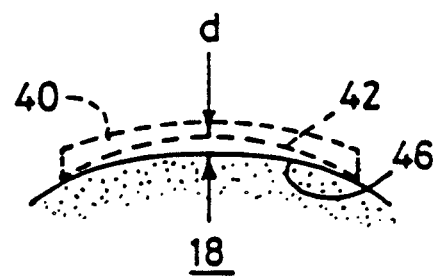
FIG. 4B illustrates diagrammatically the completion of the reprofiling operation of FIG. 4A.

FIGS. 4A and 4B illustrate the principle involved in eroding a surface to effect reprofiling thereof in accordance with the present invention. Although FIGS. 4A and 4B illustrate this principle in connection with a contact-type masking lens disposed directly upon the surface, it should be clear that the same principles are applied when a support structure is affixed to the surface and a masking means is disposed upon the support structure. Where the "lens" is convex and is to be eroded simultaneously a the surface below, it is a prerequisite that either the lens is of the so-called "contact" type, or it is supported on a transparent platform or window.

In FIGS. 4A and 4B, the reference 18 denotes the object such as the cornea of an eye to be reprofiled and, in FIG. 4A, reference 40 denotes a contact-type masking lens fitted to the eye over the area thereof to be treated. Also as indicated in FIG. 4A, the lens 40 is uniformly irradiated with a beam of radiation 12 obtained from a pulsed UV laser source.

The lens, as fitted, has a lower surface 42 of a shape matching the exising contour of the object in an upper surface which provides the desired degree of reprofiling. During the radiation, the lens 40 is gradually ablated, and an increasing area of the object becomes exposed to erosion. As indicated in FIG. 4B at the moment when the lens has been wholly ablated, the surface of the object has been eroded as indicated at 46, to the extent necessary to complete reprofiling over the area to which the lens has been fitted. As shown in FIG. 4B, the maximum thickness of the lens 40 exceed the minimum thickness by an amount equal to the maximum depth (d) of the object erosion desired.

As hereinbefore explained, the present invention is especially suited to the treatment of the cornea of an eye and provides a less dramatic means of effecting reprofiling of the cornea, for example, as a remedy for certain forms of refractive errors. FIGS. 4A and 4B illustrate the methods of the present invention in connection with the treatment of myopia (nearsightedness). Similar lenses of appropriate shape can, of course, be employed to remedy other forms of refractive errors, such as hyperopia and astigmatism.

Figure 5:
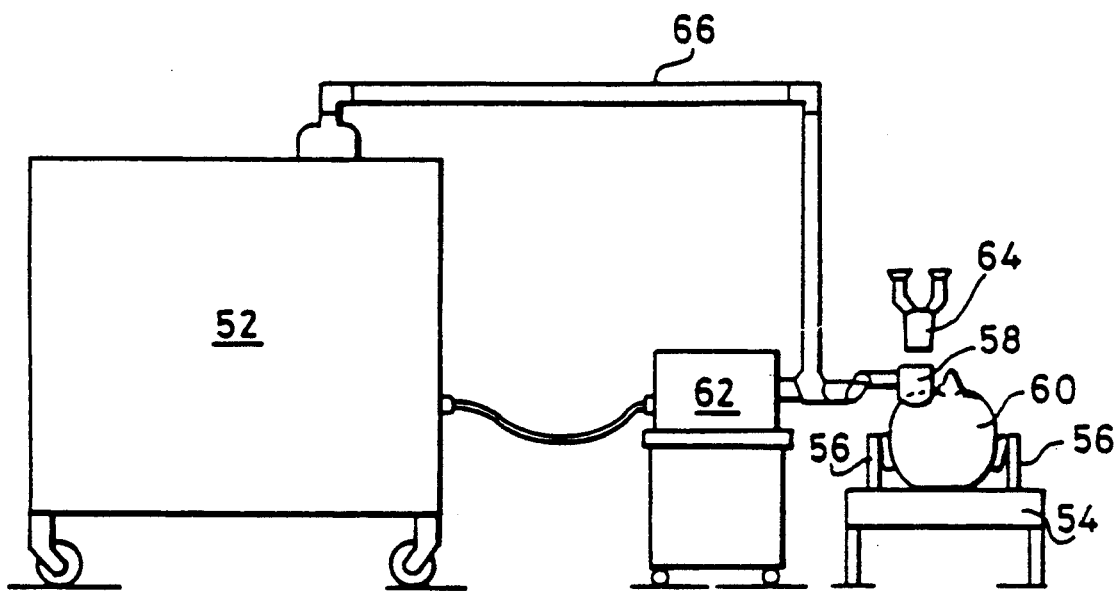
FIG. 5 shows a laser apparatus for measurement and reprofiling.

FIG. 5 illustrates an apparatus for reprofiling the cornea of a human eye in accordance with the invention. A laser and associated control circuitry is contained in a housing 52. The beam-forming optics, for providing a beam of desired shape and size, can also be contained within the housing 52 together with the laser power supply control circuits. An optical wave guide 66, which can be flexible or rigid and includes suitable mirrors, prisms and lenses, is provided to transmit the laser beam output from the housing 52 to the patient 60. The patient 60 is lying face-upwards on an operating table 54. The operating table 54 will support the patient's head against vertical movement. If desired, side supports 56 may also be provided to restrain sideways movement of the patient's head.

The erodable mask of the present invention is disposed within an eyepiece 50A adapted to fit over the patient's eye. The eyepiece 58 includes suction means for providing suction to clamp the eyepiece over the patient's eye. The eyepiece can include a cup of resiliently deformed flexible material such as rubber or plastics material which when placed over the eyeball will clamp thereto upon being evacuated. Also disposed within the eyepiece are suitable optical elements for transmitting the laser radiation to the surface of the eye, and the erodable mask similar in structure to either the erodable mask shown in FIG. 2 or FIG. 3 above. The erodable mask is manufactured as described above based on measurements of the patient's eye and has a profile which will impart the desired refraction correction upon erosion.

During the operation, the eye can be observed using a surgical microscope 64 which is supported above the patient by any convenient means. The surgical microscope 64 may be connected to the eyepiece 58, but will more normally be separated therefrom and supported by an arm (not shown) from the ceiling or by a cantilever (not shown).

A measuring device 62 can also be employed in conjunction with the present apparatus to measure the changes in the curvature of the cornea following operation. Such a measuring device 62 can also be employed to monitor the degree of erosion of the mask during treatment. The measuring device can take the form of a commercially-available keratometer or other suitable device and as shown in FIG. 5, can be connected directly to the laser optical path or may be movable when needed to occupy the position shown for the surgical microscope 64, the operator moving the measuring device 62 or the microscope 64 into position as required.

The measuring device 62 can further provide the feedback control, as shown in FIG. 1, whereby information from optical or other inspection of the surface which is being exposed to laser erosion is used to control the actual duration and amplitude of the pulses supplied by the laser and may be tuned so a to produce just the desired degree of erosion of the surface by each pulse.

Figure 6:
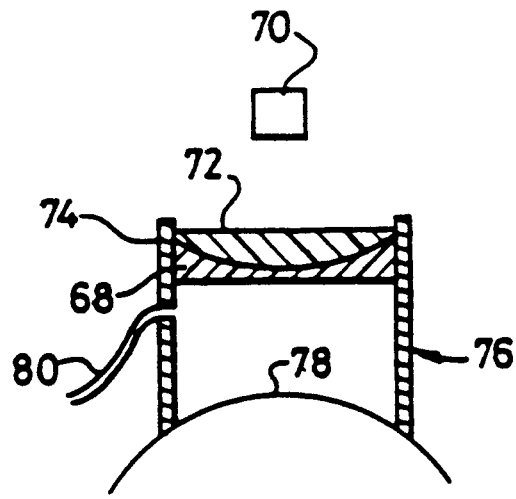
FIG. 6 illustrates a modified version of the apparatus as shown in FIG. 2, capable of retaining a liquid or gel as a convex lens-like mask.
Figure 7:
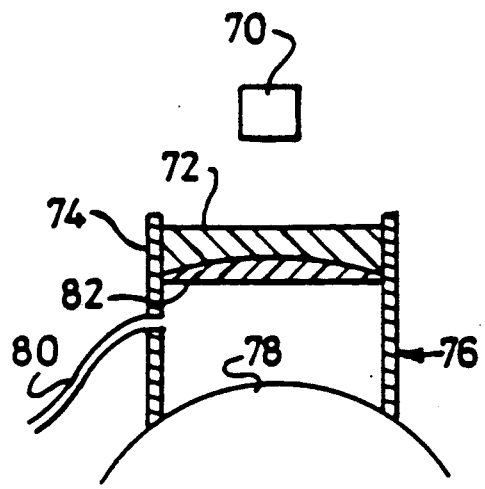
FIG. 7 illustrates a modification to the arrangement of FIG. 6 in which a concave lens-like mask of liquid or gel can be formed.

A modification is shown in FIGS. 6 and 7 which possesses two advantages:

(1) materials which are not rigid and self supporting or which heat up sufficiently during exposure to the laser pulses as to become liquid or gel-like, may be employed, (2) the need for accurately manufacturing curved elements which are then to be destroyed, can be avoided, since the curved shape is provided by the base of the tray (or well), which being transparent to the wavelengths involved, does not absorb radiation and is therefore not destroyed.

This second feature is of particular value in apparatus and methods which are to be applied to the shaping of surfaces to a uniform standard. It is of less importance when each process is a "one-time only" procedure requiring a particular shaping to be achieved - as is usually the case in corneal surgery.

To this end FIG. 6 shows a device in which a dished member 68 of a material which is transparent to radiation from a laser 70, provides a transparent support for a liquid 72. The liquid is contained by a peripheral wall 74 which is a continuation of a support ring 76 which itself rests on and is clamped to the surface 78 to be ablated by the laser radiation. A vacuum pump (not shown) is connected to the ring 76 via a tube 80, and operated to evacuate the ring, and clamp it to the surface.

The choice of the material 72 is governed by the erosion characteristics of the surface 78. Ideally the material 72 should be "eroded" at the same rate as the material forming the surface 78 so that the final shape of the surface 78 will be substantially the same as that of the surface of the dished member 68. As shown this is concavely profiled.

If a convex profile is required in the surface 78, a convexly profiled base member 82 is employed in place of the element 68 of FIG. 6. Such an element is shown in FIG. 7. In all other respects FIG. 7 is the same as FIG. 6 and the same reference numerals have been used throughout.

The material 72 may be solid, liquid or a gel. If thermoplastic or thermosetting the material may for example introduced into the tray (74, 68) or (74, 82) and heated to allow it to flow and conform to the shape of the base 68, 82.

By fitting a transparent lid, to the rim of the wall 74, a gas or vapour or volatile material may be employed as the material 72.

We claim:

1. An erodable mask for reprofiling a surface using laser radiation, the mask comprising a material erodable by laser radiation and positionable between a source of laser radiation and the surface, the mask providing a predefined profile of resistance to the said laser radiation, such that upon irradiation of the mask a portion of the laser radiation is selectively absorbed by the mask and another portion is transmitted to the surface in accordance with the mask profile, to selectively erode the surface.

2. The apparatus of claim 1 wherein the apparatus further comprises means for immobilizing the surface.

3. The mask of claim 1, wherein the mask material comprises a material selected from the group consisting of polymethylmethacrylate, polymethylstyrene and mixtures thereof.

4. The apparatus of claim 1, wherein the mask is disposed upon, and directly affixed to, the surface.

5. The mask of claim 4, wherein the mask varies in thickness to provide the predefined profile of resistance.

6. The mask of claim 4, wherein the mask varies in composition to provide the predefined profile of resistance.

7. A masking apparatus for use in laser reprofiling of corneal tissue comprising an erodable mask being erodable by radiation from a laser and capable of direct fixation upon a cornea, the mask having a predefined profile of resistance to the laser radiation, whereby upon irradiation of the mask, a portion of the laser radiation is selectively by the mask absorbed and another portion is transmitted to the cornea in accordance with the mask profile to selectively erode the tissue.

8. The apparatus of claim 7, wherein the mask varies in thickness to provide the said profile.

9. The apparatus of claim 7, wherein the mask varies in composition to provide the said profile.

10. The apparatus of claim 7, wherein the mask is fixable to the corneal surface by a suction means.

11. The apparatus as claimed in claim 7, wherein the mask is formed at least in part from a material which is ablated or eroded by the laser radiation, the said resistance being a measure of the resistance to ablation or erosion by the laser radiation.

12. The apparatus of claim 7, wherein the mask has a diameter in the range of about 3 to 12 millimeters and a maximum thickness of about 2 millimeters or less.

13. The apparatus of claim 12, wherein the mask is formed from polymethylmethacrylate, polymethylstyrene, or mixtures thereof.

14. Laser apparatus for reprofiling a surface comprising a laser means, control means for controlling the laser means to project laser radiation towards the surface, and an erodable masking means adapted to be disposed between the laser means and the surface, said masking means being erodable by the radiation from the laser means and having a predefined profile of resistance to the laser radiation, so that upon irradiation of the masking means, a portion of the laser radiation is selectively absorbed by the masking means and another portion is transmitted to the surface in accordance with the mask profile to selectively erode the surface.

15. Laser apparatus as claimed in claim 15, in which the masking means is formed from material which is ablated by absorption of the laser radiation so that the masking means is progressively destroyed during the surface reprofiling.

16. Laser apparatus as claimed in claim 14, in which the masking means comprises a tray or well of optically transparent material in which a quantity of a selected masking material can be contained.

17. Laser apparatus as claimed in claim 14, in which the material forming the masking means is selected to have similar ablation characteristics to the surface material.

18. Laser apparatus as claimed in claim 14, in which the masking means is formed from polymethylmethacrylate or polymethylstyrene or mixtures thereof.

19. Laser apparatus as claimed in claim 14, in which the masking means comprises a mask which is adapted to be disposed upon, and directly affixed to, the surface.

20. Laser apparatus as claimed in claim 19, in which the mask is constructed so as to have a first surface contoured to conform to the surface to be eroded and a second surface contoured to provide the desired surface contour following erosion by exposure to laser radiation.

21. The apparatus of claim 14, wherein the laser means is a pulsed excimer laser.

22. The apparatus of claim 21 wherein the excimer laser is an Argon-Fluoride laser operating at a wavelength of about 193 nanometers.

23. A method of reprofiling a surface comprising:
locating a laser means relative to a surface, the laser means being operable to deliver laser radiation to the surface; and
disposing an erodable masking means between the laser means and the surface, the masking means being erodable by radiation from the laser means and having a predefined profile of resistance to the laser radiation, and
irradiating the masking means, whereby a portion of the radiation is selectively absorbed by the masking means and another portion is transmitted to the surface, in accordance with the mask profile, to selectively erode the surface.

24. A method as claimed in claim 23 wherein the step of locating a laser means relative to a surface further comprises locating the laser means relative to a cornea of the eye.

25. A method as claimed in claim 23 wherein the step of locating a laser means relative to a surface further comprises locating the laser means relative to a biological tissue such as a ligament or a cartilage in a bone.

26. A method as claimed in claim 23, wherein the method further includes varying the thickness of the masking means to provide the profile of resistance.

27. A method as claimed in claim 23, wherein the method further includes varying the composition of the masking means to provide the profile of resistance.

28. A method as claimed in claim 23, wherein the step of irradiating the masking means further includes irradiating the masking means with a pulsed laser means.

29. A method as claimed in claim 28, wherein the step of irradiating the masking means further includes irradiating the masking means with a single pulse which is set to erode a depth in the range 0.1 to 1 micrometer of surface material.

* * * * *